US006423703B1

United States Patent
Joly et al.

(10) Patent No.: US 6,423,703 B1
(45) Date of Patent: Jul. 23, 2002

(54) USE OF A PORPHYRIN FOR PRODUCING A MEDICINE REDUCING THE NUMBER OF EOSINOPHILS

(75) Inventors: Francine Joly, Paris; Beauvais Francis, Sevres, both of (FR)

(73) Assignee: Sephra S.A.R.L. (FR)

( * ) Notice: Subject to any disclaimer, the term of this patent is extended or adjusted under 35 U.S.C. 154(b) by 0 days.

(21) Appl. No.: 09/673,180

(22) PCT Filed: Apr. 7, 1999

(86) PCT No.: PCT/FR99/00804

§ 371 (c)(1),
(2), (4) Date: Nov. 21, 2000

(87) PCT Pub. No.: WO99/52527

PCT Pub. Date: Oct. 21, 1999

(30) Foreign Application Priority Data

Apr. 8, 1998 (FR) ............................................. 98 04381

(51) Int. Cl.[7] ........................ A01N 55/02; A61K 31/555
(52) U.S. Cl. ........................ 514/185; 514/863; 514/826
(58) Field of Search ................................ 424/400, 9.32, 424/78.05, 641, 643, 642; 540/145, 201; 514/185, 863

(56) References Cited

U.S. PATENT DOCUMENTS

| 4,393,701 A | * | 7/1983 | Fujii et al. | 424/274 |
| 4,829,984 A | * | 5/1989 | Gordon | 600/12 |
| 5,612,019 A | * | 3/1997 | Gordon et al. | 424/9.32 |
| 5,651,993 A | * | 7/1997 | Edelson et al. | 424/534 |

FOREIGN PATENT DOCUMENTS

EP 0278681 8/1988

OTHER PUBLICATIONS

XP–002088066 Anti–Inflammatory . . . Disodium. vol. 37, No. 3–4 pp. 273–283 1992.

* cited by examiner

*Primary Examiner*—Jose G. Dees
*Assistant Examiner*—Sharmila S. Gollamudi
(74) *Attorney, Agent, or Firm*—Bierman, Muserlian and Lucas

(57) ABSTRACT

Use of zinc protoporphyrin IX and its salts to reduce the number of eosinophils in tissues, particularly for treating hypereosinophilia such as bronchial asthma, atopic dermatitis, allergic rhinitis and allergic conjunctivitis.

7 Claims, 3 Drawing Sheets

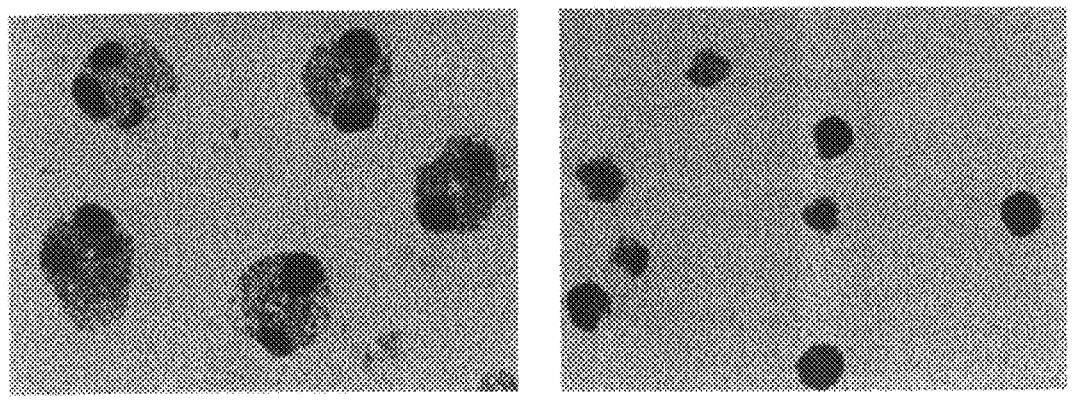
FIG. IA            FIG. IB
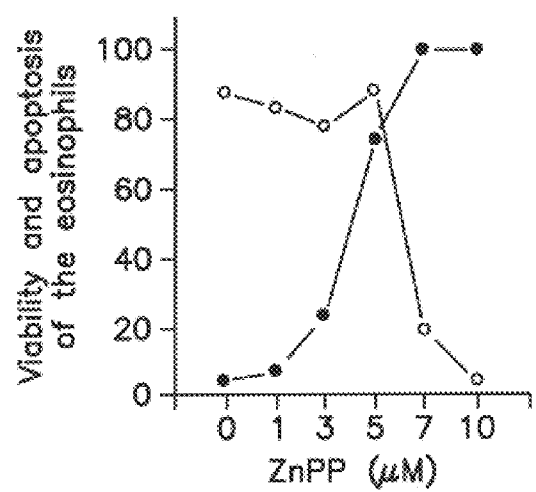
FIG. 2

USE OF A PORPHYRIN FOR PRODUCING A MEDICINE REDUCING THE NUMBER OF EOSINOPHILS

This application is a 371 of PCT/FR99/00804 filed Apr. 7, 1999.

The presents invention relates to the domain of chemistry and more particularly to that of human or veterinary therapeutic chemistry.

The present invention especially concerns the use of porphyrin for the production of a medicine lowering the number of eosinophils.

In fact, many illnesses or pathologies are connected with hypereosinophilia; amongst them, bronchial asthma can be particularly cited.

The morbidity of this illness remains significant. In France the number of people affected by asthma is calculated at 2.5 million, and the number of deaths directly attributable to asthma is 2000 per year (cf. Epidemiological study of the European Community Respiratory Health Survey). The prevalence of asthma thus remains worrying, whatever is the age and geographical location of the population studied, The treatment of chronic asthma—apart from acute attacks—is mainly dominated by the use of β2-stimulants and corticosteroids administered by inhalation. Antihistamines are only marginally used today. Each category of medicines causes a different type of effect:

The β-stimulant agents essentially cause the relaxation of the smooth bronchial muscles: they also reduce the liberation of mediators. These substances including adrenaline, isoproterenol as well as more selective substances of the β2 receptors (bronchial tubes) than the β1 receptors (heart). After inhalation, the β2 (β2-adrenergic) substances act very quickly (in several minutes) but are only active for several hours.

The principle mode of action of theophylline is the relaxation of the smooth bronchial muscle. It inhibits the delayed phase of allergy and inhibits the liberation of inflammation mediators by mastocytes. Many authors consider that it is currently the most effective maintenance treatment for asthma. One of its major drawbacks however, is its narrow therapeutic margin.

Corticosteroids inhibit the migration of granulocytes towards the sites of allergic reaction, and prevent the liberation of inflammation mediators. In particular, when they are administered in aerosols, they inhibit the delayed phase of the allergy (but not the immediate phase) and the resulting bronchial hyperactivity. Although they are very effective, the systematic administration of corticosteroids has to be reserved for difficult cases because of their secondary effects. Inhaled steroids are used for maintenance treatment but not for acute asthma attacks.

Sodium cromoglycate and nedocromil are used as a preventive measure. They inhibit the liberation of mediators and reduce bronchial hyperactivity. Cromoglycate appears to be most effective in children and certain adults, for the maintenance treatment.

Subcutaneous specific desensitisation has been used for almost a hundred years; however the way it works is still not completely understood. The injection of allergens must be carried out under medical supervision. The results of desensitisation are controversial and only appear to improve the condition of a fraction of asthmatic people.

Anti-leukotrienes are currently the cutting edge in the domain of new therapies for asthma. The leukotrienes are synthesised by the inflammation cells. They play a role in the recruitment of inflammation cells and in bronchoconstriction. A number of molecules capable of inhibiting the effect of leukotrienes are currently being developed. Two of them, zafirlukast and pranlukast, are antagonists of the leukotriene receptors, but their use remains limited to moderate cases of asthma.

The importance of phosphodiesterases inhibitors, the main one being theophylline, is currently being rediscovered. The developed drugs currently attempt to inhibit more specifically phosphodiesterase of type IV, preponderantly present in the inflammation cells (eosinophils, lymphocytes) and the smooth bronchial muscles. The second-generation theophyllines are better able to be tolerated than theophylline itself, whose therapeutic margin remains narrow.

Furthermore, monoclonal antibodies directed against IL-5 are developed in the aim of controlling hypereosinophilia and the bronchial hyperreactivity of asthma. Even so, anti-IgE monoclonal antibodies are developed in the aim of blocking the IgE responsible for the sensitisation of the allergy cells. However, the effectiveness of these products in human asthma still has to be proven.

Asthma has been defined as "a chronic inflammatory illness of the airways, responsible for attacks of wheezing, a reduction of the MEVS (Maximum exhalation volume per second) and bronchial hyperreactivity" (NIH workshop report, January 1995). Bronchial hyperreactivity is the tendency that the bronchial tubes in asthmatics have to contract under the influence of a number of irritant or pharmacological stimuli, which are without effect in a healthy subject.

The most spectacular characteristic of the histopathology of asthma is the very large infiltration of eosinophils, macrophages and lymphocytes into the bronchial mucous membranes. Eosinophils appear to be the key cells responsible for lesions of the bronchial mucous membranes and bronchial hyperreactivity, although the precise mechanism of these phenomena is still being discussed.

Recent studies have compared asthmatics with healthy volunteers by using the broncho-alveolar wash technique and carrying out bronchial biopsies. A high number of eosinophils, both in the bronchial mucous membranes and in the broncho-alveolar wash fluid, is characteristic of asthma. Blood hypereosinophilia and the presence of eosinophils in the sputum, are characteristic of asthma; the level of eosinophils in the blood is correlated to the level of bronchial hyperreactivity.

After their differentiation and maturation in the bone marrow, the mature eosinophils are liberated into the blood circulation and go on to their main location in the tissues. The life span of the eosinophils in the tissues is unknown, but it is estimated at at least several days and it is probably dependent on the presence of cytokines like IL-5, IL-3 or GM-CSF. In some tissues (Skin, lung), the eosinophils are physiologically rare, but they can migrate to these tissues where they display their cytotoxic function and liberate inflammation mediators in response to a suitable stimulus [Texeira et al, 1995, Tr. Pharmacol. Sc. 16:418–423].

Eosinophils contribute to the physiopathology of allergic illnesses, particularly in the skin, the lungs, the nasal and ocular mucous membranes [Corrigan et al, 1992, Immunol. Today 13:501–506].

The accumulation in the tissues of eosinophils during allergic illnesses can prove to be disastrous; in fact, the granular proteins of the eosinophils are cytotoxic for the bronchial epithelial cells and also have many effects on the mastocytes, the epithelial cells, the macrophages and the T cells. Many works stress the link between the number of eosinophils, their state of activation and the severity of the asthma, both in man and animals (Bousquet et al, 1990, N Engl. J. Med. 323:1033–1039; Roisman et al, 1995, J. Clin. Invest. 96:12–21).

However despite the progress made in the course of the last few years, in the understanding of the mechanisms of allergy in general and asthma in particular, the most used medicines today belong to therapeutic classes which have been available for decades and the new molecules on the market continue to be based on old concepts.

According to the present invention, the proposed medicine is based on a different concept, that of preventing the accumulation of eosinophils in the tissues by pharmacologically acting on their life span. In fact, having the possibility of pharmacologically modulating the life span of the eosinophils is essential as it affects the potential of the eosinophil to liberate mediators, to exert its cytotoxicity or to functionally co-operate with other cells. Cytokine IL-5 appears to play a very important role in the survival in vivo of the eosinophils. It is however pharmacologically worthwhile to inhibit the effects of IL-5 and other factors for the survival of the eosinophils. This pharmacological modification of the life span of eosinophils has been little explored until now.

U.S. Pat. Nos. 5,510,339 and 5,631,267 (Gleich et al) concern the use of lidocaine as well as other local anaesthetics in the treatment of asthma. These authors indicate that in vitro lidocaine and other local anaesthetics reduce the survival of eosinophils. The inhalation of lidocaine thus makes possible the reduction of glucocorticoids inhaled, in asthmatics.

In the absence of survival factors (IL-5, IL-3 or GM-CSF . . . ), the eosinophils in culture in vitro quickly die (in 48–72 hrs) by an active phenomenon of "programmed cellular death" which has the characteristics of apoptosis. Apoptosis is the opposite of necrosis which results in a massive attack of the cell leading to cellular lysis thus accompanying inflammatory phenomena. In the course of apoptosis, on the other hand, cellular homeostasis continues and membrane integrity is maintained. The apoptotic cell is rapidly recognised (because of the expression of certain membrane antigens) and phagocytized by macrophages or by surrounding cells. The apoptotic cell therefore plays a role in its own death ("cellular suicide").

So, the induction of the "programmed cellular death" of the eosinophils (apoptose) is not accompanied by inflammation and on the contrary suppresses the inflammation linked with tissue hypereosinophilia; that is why the pharmacological induction of the death of the eosinophils by apoptosis is a worthwhile process. The direct consequence of the induction, of the apoptosis of the eosinophils is the reduction of the number of eosinophils in the tissues.

However, the pathways of intracellular signals which lead cells to apoptosis are shared by many cells. So, the problem that arises is how to specifically induce the apoptosis of the eosinophils without inducing that of the cells of the respiratory epithelium and mucous membranes, and consequently without being toxic for the body.

In a surprising manner it has been found according to the present invention that Zinc-Protoporphyrin IX (ZnPP-IX) has the property of inducing the eosinophils without being toxic for the body.

ZnPP-IX is a natural molecule that is particularly present in the red blood cells. Its main chemical characteristics are the following:

Appearance: dark red

Molecular weight: 626.1

Basic formula: $C_{34}H_{32}N_4O_4Zn$

Storage: −20° C., stable for at least 1 year—protected from light and humidity—

Solubility: in ethanol (10mg/ml), DMSO (20mg/ml), very soluble in aqueous alkaline solutions Formula developed:

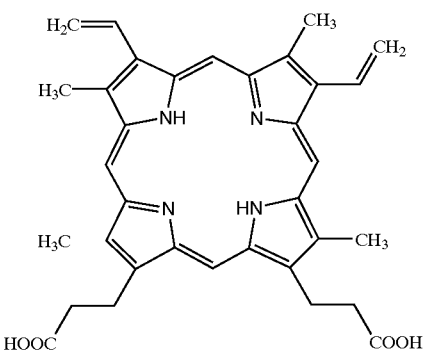

No toxicity has been reported in animals as far as ZnPP-IX is concerned.

Table I below gives the toxicity of ZnPP-IX and the doses used in the litterature (in vivo animal studies). Three species were used: rats, mice and monkeys. Several methods of administration were used: intravenous (i.v.), intraperitoneal (i.p.) and sub-cutaneous. No harmful effects were revealed.

| References | Admin | Dose | Duration | Pharmacological effects | Species |
| --- | --- | --- | --- | --- | --- |
| Rodgers et al, 1990 | i.v. | 25 mg/kg | 26 hrs | Reduces neonatal jaundice | Rhesus monkeys (new-born) |
| Kadoya et al, 1995 | i.p. | 50 mg/kg | 24 hrs | Protects from cerebral ischemia | Adult rats |
| Rodgers et al, 1996 | i.p. | 25 mg/kg | 21 days | Reduces neonatal jaundice | New-born rats |
| Trakshel et al, 1992 | s.c. | 31 mg/kg (2x −4j) | 7 days | No effect on steroidogenesis | Rats |
| Vreman et al, 1990 | i.v. | 25 mg/kg | 24 hrs | Reduces hyperbilirubinemia due to iatrogenic hemolysis | Rhesus monkeys (new-born) |
| Qato et Maines, 1985 | s.c. | 25 mg/kg | 12 days | Reduces neonatal jaundice | Rhesus monkeys and cynomolgus |
| Nagai et al, 1992 | | 30 mg/kg | | Anti-inflammatory effect | Adult rats and mice |
| Zhao et al, 1996 | i.p. | 50 mg/kg | 24 hrs | Protects from cerebral ischemia | Adult rats |
| Hintz et al, 1990 | i.p. | 37 mg/kg | 12 hrs | No phototoxic effect | New-born rats |

-continued

| References | Admin | Dose | Duration | Pharmacological effects | Species |
|---|---|---|---|---|---|
| Dennery et al, 1993 | i.p. | 25 mg/kg | 3 hrs | Neither lipid peroxydation, nor phototoxicity during phototherapy | New-born rats |
| Vrema et al, 1988 | p.o. | 25 mg/kg | 6 hrs | No inhibitory effect on intestinal, splenic and hepatic hemoxygenesis | New-born and adult rats |

The present invention therefore specifically concerns the use of Zinc-Protoporphyrin IX (ZnPP-IX) or one of its salts, for the production of a medicine intended to reduce the number of eosinophils in the tissues.

Zinc-Protoporphyrin IX (ZnPP-IX) can be used for example as a disodic derivative.

Amongst the pathologies linked to hypereosinophilia, bronchial asthma, atopic dermatitis, allergic rhinitis and allergic conjunctivitis can be cited.

In fact the physiopathology of allergic rhinitis and asthma are one and the same. In both cases it is the recruitment of-eosinophils in the respiratory tissues.

Allergic conjunctivitis is often linked with allergic rhinitis. Although it is less studied on a fundamental level than asthma and allergic rhinitis the importance of the mastocyte-eosinophil coupling in allergic rhinitis is stressed. During atopic dermatitis, there is a massive recruitment of eosinophils in the dermis. There are massive deposits of cationic proteins from the eosinophils and relatively few intact eosinophils (Leiferman K. M., J. AM. Acad. Dermatol. 1991, 24: 1101–1112). In fact, they undergo lysis very rapidly (necrosis).

According to the invention, therefore, Zinc-Protoporphyrin IX (ZnPP-IX) is used for the production of a medicine intended to treat pathologies linked to hyper-eosinophilia.

More specifically, ZnPP-IX is used according to the invention for the production of a medicine intended to treat bronchial asthma, atopic dermatitis, allergic rhinitis, and allergic conjunctivitis.

ZnPP-IX could be used in association with any other active ingredient intended to treat the pathologies linked to hypereosinophilia. Examples of such active ingredients are corticosteroids, β2-mimetic agents, antileukotriene, lipoxygenase inhibitors, PAF-acether antagonists, synthetic PAF-acether inhibitors, synthetic prostaglandin inhibitors, anti-H1, anti-degranulation agents like sodium cromoglycate, the antagonists of substance P, VIP, bradyknin, CGRP, the antagonists of IL-5 and the anti-IL-5 monoclonal antibodies, or any immunotherapeutic treatment allergenic or otherwise. ZnPP-IX is used in association with inert, non-toxic, pharmaceutically acceptable excipients or vehicles, allowing oral, topical, parenteral, nasal or bronchial administration. ZnPP-IX can be used in the form of an aqueous solution or suspension, or in a dry state, in plain or sugar coated tablets, soft gelatine capsules, capsules, powders. For asthma, the preferred method of administration is by inhalation.

As a general rule, the content in ZnPP-IX can vary from 0.050 mg to 5000 mg per unit dose.

BRIEF DESCRIPTION OF THE DRAWINGS

FIG. 1 is a visual view under the fluorescence microscope.

FIG. 2 is a graph of the dose-dependent activity of ZnPP-IX.

EXPERIMENTAL SECTION

EXAMPLE I

Figure 3:
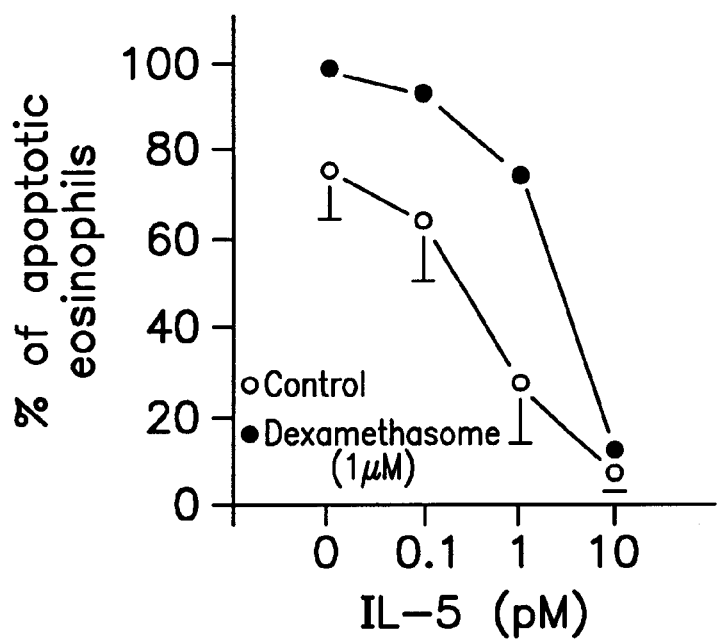
FIG. 3 is a graph of the percentage of a apoptodic esoinophils induced by dexamethasone.

Reduction in the Survival and Induction of Apoptosis in vitro of Human Eosinophils by ZnPP-IX Experimentally, apoptotic cells can be recognised by a certain umber of criteria:

fragmentation of DNA due to the activation of endonucleases: this gives the apoptotic cells a characteristic "ladder-like" appearance in the electrophoresis of DNA;

Reduction in cellular volume and condensation of the cytoplasm and cytoplasmic organites; pycnotic appearance of the nucleus and chromatin; finally, or at least in the initial period of apoptosis in vitro, the apoptotic cells expel the blue trypan, unlike necrosed cells.

1) Method a) Purification of Eosinophils via the Immuno-magnetic Method

A leukocyte-rich suspension is obtained after sedimentation of whole blood, anticoagulated in the presence of dextran T500 (4.5%). 35 ml of aliquots are added to 15 mi of Ficoll. After centrifugation (30 min, 1000×g) the mononucleated cells at the interface are eliminated. The pellet which contains neutrophils, eosinophils and the corpuscles is washed and subjected to an osmotic shock in order to eliminate the corpuscles. The magnetic cellular separation system (MACS; Miltenyi Biotec) is used to purify the eosinophils by negative selection [Hansel et al, 1991, J. Immunol. Meth. 145: 105–110]. Magnetic particles anti-CD16 (1 $\mu l/1 \times 10^6$ cells) are added to the suspension of neutrophils and eosinophils at 4° C. and kept at this temperature for 40 minutes with several placement gain in solution. The suspension is then added at the summit of the separation column in the presence of a magnetic field, the tap open at the base. 30 ml of PBS/FCS is passed through the column and the effluent is recovered. The magnetically marked cells (neutrophils) remain in the column; the unmarked cells (eosinophils) are recovered in the effluent and washed. PBS=Phosphate buffered saline FCS=Foetal calf serum b) Culture of the Surviving Eosinophils The freshly purified eosinophils are again placed in suspension (1.5–3×$10^5$ cells per ml) in RPMI 1640 (Gibco BRL) supplemented with 0.1 mM non essential amino acids, 100 U/ml of penicillin, 10 $\mu g$ of streptomycine, 10 mM of HEPES, 2 mM of glutamine and 10% FCS. The aliquots of 160 $\mu l$ of cellular suspension are deposited in each of the wells of a 96 well tray (Costar) containing 20 $\mu l$ of IL-5 as survival factor. Twenty $\mu l$ of the substance to be studied in a precise concentration or 20 $\mu l$ of the medium on its own as a control are deposited in the corresponding wells. The cellular viability and the percentage of apoptotic eosinophils are counted at 24 hrs and 48 hrs with the aid of the methods below.

c) Evaluation of the Survival and the Apoptosis of Eosinophils in vitro

Blue trypan makes it possible to evaluate cellular viability. The cellular suspension is added to an equal volume of blue trypan at 0.1% in PBS. The absolute number of cells excluding the blue trypan (="living" cells) per unit volume is obtained by counting the cells in a hemocytometer (Mallassez).

Cytology: makes it possible to visualise the morphological modification of the eosinophils during apoptosis in vitro. The cellular suspension is cyto-centrifuged then the strips are coloured (kit RAL 555, Prolabo). The percentage of apoptotic cells is established by optical microscope according to their characteristic morphology (pyknotic nucleus with condensed chromatine or without a nucleus, reduction in the cells diameter, cytoplasmic condensation). The freshly isolated eosinophils from the blood circulation have a characteristic morphology in optical microscopy: a granular cytoplasm coloured red-orange by eosin and a very often bivobed nucleus. In the absence of survival factors such as IL-5, IL-3 or GM-CSF, the first morphological signs of apotosis of the eosinophils appear. The chromatin condenses and the nucleus of the eosinophil takes on a pyknotic appearance. This pyknotic appearance of the nucleus, standard in the course of apoptosis, is however rarely observed in the eosinophil, perhaps because of its brevity. Another morphological sign characteristic of apoptosis is the reduction of cellular volume which is very marked in the eosinophil (Beauvais et al, 1995, J, Leukoc. Biol. 57: 851–855). After 48 hours of incubation, the nuclear structures have disappeared in the majority of eosinophils which now appear in the form of anucleated vesicles. The eosinophils which have been incubated in the presence of lnterleukine-5 do not undergo any apoptosis and their morphology (at 48 hrs) is very close to that of freshly withdrawn eosinophils.

Tunel Method (DNA Fragmentation in situ)

The TUNEL method makes it possible to visualise the apoptotic nuclei containing the fragmented DNA. Its assumption rests on the enzymatic fixation of a fluorescent marker (Fluoresceine-12-dUTP) at the free extremities of the DNA (3'-OH DNA). This technique consists of the cells in each well being cytocentrifuged then fixed by formaldehyde solution at 4% (25 min at 4° C.). After washing, the preparations are made permeable by a solution of Triton X-100 0.2% (5 min at 20° C.). The cells are incubated (1 hr at 37° C.) in the presence of a solution containing fluoresceine-12-dUTP and the enzyme TdT (terminal deoxynucleotidal transferase). The reaction is kept in a stopping solution. After mounting under a coverglass, the preparation is visualized under the fluorescence microscope (Apoptosis Detection System Fluorescein. Promega, Madison, Wis., USA).

2) Results a) Induction of in vitro Apoptosis of the Eosinophils by ZnPP-IX

In order to test the effect of Zn-Protoporphyrin IX on the apoptosis of eosinophils, ZnPP-IX was incubated in the presence of eosinophils kept alive by IL-5.

TABLE II

Apoptosis of eosinophils induced by Zn-Protoporphyrin-IX (10 μM)
(average of three experiments)

|  | 0 | 24 hrs | 48 hrs |
|---|---|---|---|
| 0 | 0 | 23 ± 1 | 94 ± 2 |
| ZnPP | 0 | 45 ± 15 | 99 ± 1 |
| IL-5 | 0 | 2 ± 2 | 2 ± 1 |
| IL-5 + ZnPP | 0 | 3 ± 2 | 99 ± 1 |

The eosinophils are incubated in RPMI 1640 for 48 hrs in the presence or not of IL-5 (10 pM) and ZnPP-IX (10μ).

In the absence of IL-5, ZnPP-IX accelerates the apoptosis of the eosinophils. In the presence of IL-5 and ZnPP-IX, the number of apoptotic cells is very small at 24 hrs but at 48 hrs, practically all the cells are apoptotic.

FIG. 1 shows the appearance of the eosinophils at 48 hrs according to whether they have been placed (cf.B) or not (cf.A) in the presence of ZnPP-IX.

A:eosinophils+IL-5 (10 pM)–48 hrs

B:eosinophils+IL-5 (10 pM)+ZNPP-IX (10 μM)–48 hrs

FIG. 2 illustrates the dosedependant activity of ZnPP-IX on the survival and apoptosis of the eosinophils. (the average of two representative experiments)

b) Nuclei of the Apoptotic Eosinophils Highlighted by the Tunel Method

The eosinophils are kept alive in the presence of IL-5 (lpM) and ZnPP-IX (10 μM) or a control solution): during 48 hours. In the presence of IL-5 and the control solution, there is no marking of the nuclei. On the other hand, in the presence of IL-5 and ZnPP-IX, the apoptotic nuclei, easily recognisable by their pyknotic appearance, appear marked.

c) Comparison of the Effects of ZnPP-IX on the Apoptosis of the Eosinophils with those of Dexamethasone Dexamethasone is a powerful inductor of the apoptosis of eosinophils. FIG. 3 illustrates the percentage of apoptotic eosinophils induced by dexamethasone in function of the quantity of cytokine IL-5 (pM). It has been noticed that the higher the concentration of IL-5 is, the less the dexamethasone induces apoptosis in the eosinophils. Therefore, at the higher concentrations of IL-5 used, dexamethasone has no effect on apoptosis. The phenomenon observed with IL-5 is equally so with other cytokines like GM-CSF and IL-3.

These results indicate that the eosinophils are much more "protected" form the effects of glucocorticoids than they are in an environment rich in survival factors, as is the case for example in the Inflammatory sites. On the other hand, as we have seen, ZnPP-IX induces the apoptosis of eosinophils in stronger concentrations of IL5 (10 pM) and thus succeeds where dexamethasone fails.

EXAMPLE II

Test of the Effect of ZnPP-IX in an Animal Model of Hypereosinophilia

The effect of ZnPP-IX has been studied on peritoneal hypereosinophilia in mice.

Method

Peritoneal Hypereosinophilia

Hypereosinophilia is Induced by Ovalbumin a) Immunisation and Induction of Peritoneal Hypereosinophilia Swiss mice (about 20 g) are immunised sub cutaneously twice (with a 6 day interval) with 100 μg of ovalbumin in 0.4 ml of a suspension at 4 mg/ml of Al(OH)$_3$ in NaCl 0.9%. One week after the second injection, 0.2 ml of ovalbumin at 5 μg/ml of ovalbumin are administered by intraperitoneal injection. The control mice are injected with the vehicle only.

b/Quantification of the Inflammatory Infiltrate

The mice are killed at different times (overdose of ether) and—after dissection—undergo a peritoneal wash with 6ml of NaCl 0.9% (heparinised). After slight massage, the liquid of the wash is collected and the cellular concentration is measured in a hemocytometer. Cytocentrifugation strips are made and coloured by the Wright colorant (kit RAL 555, Prolabo, France). The differential count of mononucleated (monocytes+macrophages+lymphocytes), eosinophil and neutrophil cells is carried out objectively×100 by immersion in oil. During the peritoneal washing of the control mice, the residual cells are essentially macrophages, whereas during the peritoneal washing of mice immunised by ovalbumin, an inflammatory infiltrate with the apparition of polynuclear eosinophils and neutrophils is observed.

Figure 4:
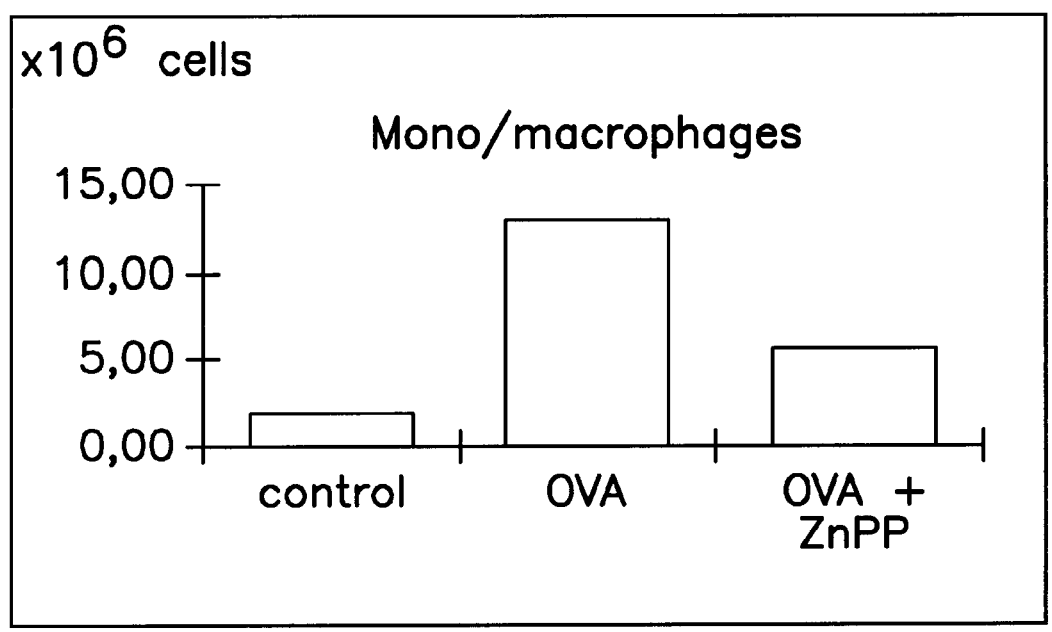
FIGS. 4 to 6 are bar graphs of the results of the test reported on pages 10 and 11.
Figure 5:
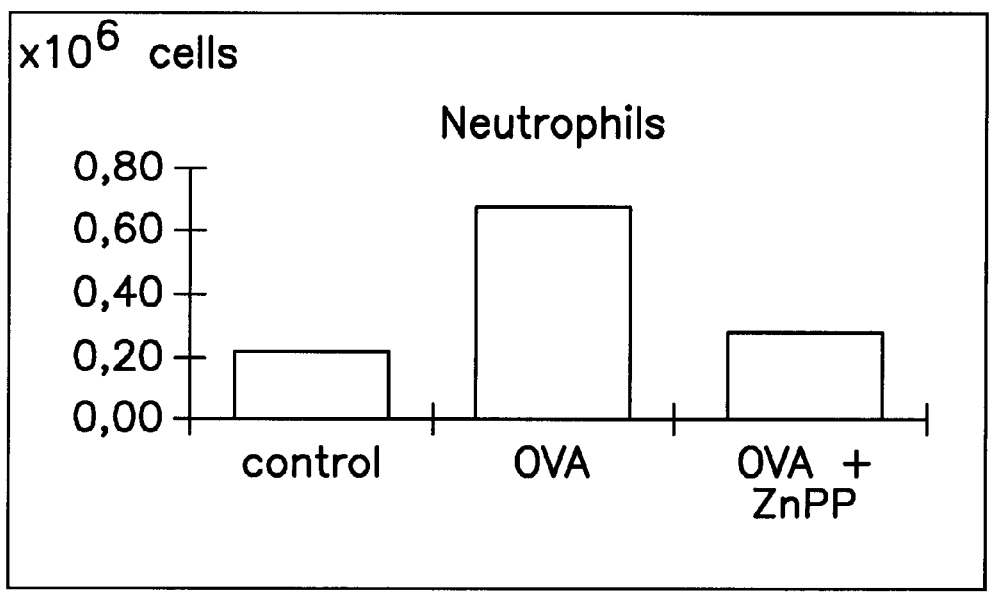
Figure 6:
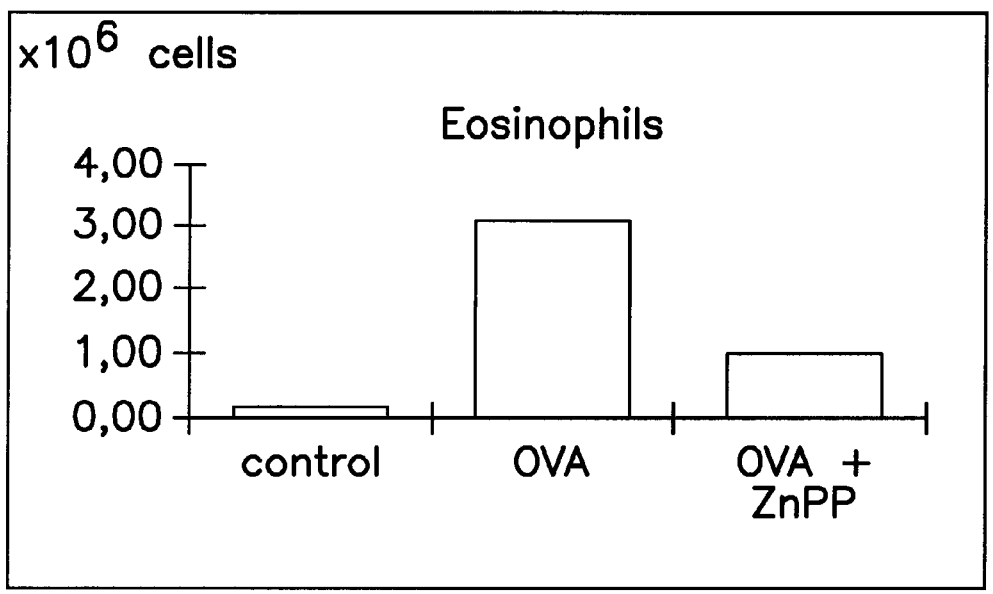

The ZnPP-IX is Injected at the same time as the second injection of ovalbumin (OVA). Each mouse receives 0.1 ml of ZnPP-IX to 1 mM (62.3 μg per mouse or 3.1 mg/kg) by intraperitoneal administration. The results are represented by FIGS. 4, 5 and 6. Each column represents the average for two mice at 48 hrs.

In conclusion, ZnPP-IX reduces the inflammatory infiltrate, through a large decrease in the number of eosinophils in the tissues.

EXAMPLE III

Example of the Production of a Medicine Based on Zinc Protoporphyrin IX

| Powder for inhalation in capsules | |
| --- | --- |
| ZnPP-IX (disodium salt) | 50 mg |
| Lactose | 100 mg |

Capsule Coating: Gelatine

What is claimed is:

1. A method of treating pathologies connected to hypereosinophilia in humans comprising administering to humans in need thereof an amount of Zinc-Protoporphyrin IX (ZnPP-IX) without toxicity sufficient to treat said pathologies, said pathologies connected to hypereosinophilia in humans is selected from the group consisting of bronchial asthma, atopic dermatitis, allergic dermatitis, and allergic conjunctivitis.

2. The method of claim 1 wherein the cells of the mucous membranes and respiratory epithelium are not effected.

3. The method of claim 1 wherein the ZnPP-IX is in the form of a disodium salt.

4. The method of claim 1 wherein the method of administration is selected from the group consisting of oral, parenteral, nasal and bronchial.

5. The method of claim 1 wherein the dosage is 0.05 to 5000 mg of ZnPP-IX.

6. The method of claim 1 wherein the amount of ZnPP-IX is effective to reduce the number of eosinophils without inducing toxicity.

7. The method of claim 1 wherein ZnPP-IX or one of its salts is combined with at least one active ingredient intended to treat pathologies connected to hypereosinophilia, selected from the group consisting of corticosteroids, β2-mimetic agents, anti-leukotriene agents and lipoxygenase inhibitors.

* * * * *